United States Patent
Brabrand

(10) Patent No.: US 7,801,583 B2
(45) Date of Patent: Sep. 21, 2010

(54) EXTRAVASATION DETECTOR

(75) Inventor: Knut Brabrand, Rasta (NO)

(73) Assignee: Neorad AS, Oslo (NO)

( * ) Notice: Subject to any disclaimer, the term of this patent is extended or adjusted under 35 U.S.C. 154(b) by 1047 days.

(21) Appl. No.: 10/730,919

(22) Filed: Dec. 10, 2003

(65) Prior Publication Data

US 2004/0176690 A1    Sep. 9, 2004

Related U.S. Application Data

(60) Provisional application No. 60/432,256, filed on Dec. 11, 2002.

(30) Foreign Application Priority Data

Dec. 10, 2002    (GB)    ................................ 0228770.4

(51) Int. Cl.
    *A61B 5/00*    (2006.01)
(52) U.S. Cl. .................. 600/382; 600/547; 600/384; 600/437
(58) Field of Classification Search ......... 600/437–456, 600/464, 500–504, 507, 407, 425, 547, 382; 600/384, 393; 604/65, 66, 253, 272, 503, 604/900; 382/131
    See application file for complete search history.

(56) References Cited

U.S. PATENT DOCUMENTS

| | | | | |
|---|---|---|---|---|
| 4,378,808 A | * | 4/1983 | Lichtenstein | ................ 600/549 |
| 4,534,756 A | * | 8/1985 | Nelson | ....................... 604/505 |
| 4,647,281 A | | 3/1987 | Carr | ............................. 604/50 |
| 4,651,742 A | | 3/1987 | Namekawa et al. | ......... 128/663 |
| 4,877,034 A | * | 10/1989 | Atkins et al. | ................. 600/475 |
| 5,007,428 A | | 4/1991 | Watmough | ............. 128/660.04 |
| 5,026,348 A | * | 6/1991 | Venegas | ..................... 604/122 |
| 5,233,994 A | | 8/1993 | Shmulewitz | ............ 128/661.08 |
| 5,334,141 A | * | 8/1994 | Carr et al. | ................... 604/503 |
| 5,840,026 A | * | 11/1998 | Uber et al. | .................. 600/431 |
| 5,947,910 A | * | 9/1999 | Zimmet | ...................... 600/547 |
| 5,964,703 A | * | 10/1999 | Goodman et al. | ........... 600/382 |

(Continued)

FOREIGN PATENT DOCUMENTS

WO    WO 99/15074    4/1999

(Continued)

*Primary Examiner*—Long V Le
*Assistant Examiner*—Sanjay Cattungal
(74) *Attorney, Agent, or Firm*—Finnegan, Henderson, Farabow, Garrett & Dunner, L.L.P.

(57) ABSTRACT

Ultrasound Doppler probe 2 is placed above the vein downstream of the infusion site. Processor 4 converts the output from the probe 2 into a form that may be displayed as an image on display unit 5. It also determines whether the velocity corresponds to a flow of contrast medium along the vein. If the cannula 13 is properly sited and the contrast medium flows as desired along the vein, this will lead to an increased flow velocity in the vein. This is detected by ultrasound probe 2 and, as described above, the processor unit 4 will therefore determine that no extravasation has occurred. However, where extravasation of contrast medium occurs this results in a low or zero velocity output from the probe 2 from which the processor unit 4 determines that extravasation has occurred. It therefore immediately sends a "stop" signal to pump controller 11 which stops pump 10.

18 Claims, 4 Drawing Sheets

U.S. PATENT DOCUMENTS

| | | | |
|---|---|---|---|
| 6,347,242 B1 * | 2/2002 | Friedlander | 600/431 |
| 6,375,624 B1 * | 4/2002 | Uber et al. | 600/549 |
| 6,408,204 B1 * | 6/2002 | Hirschman | 600/547 |
| 6,425,878 B1 * | 7/2002 | Shekalim | 604/65 |
| 6,585,675 B1 * | 7/2003 | O'Mahony et al. | 604/4.01 |
| 6,796,955 B2 * | 9/2004 | O'Mahony et al. | 604/6.11 |
| 2002/0016547 A1 * | 2/2002 | Bang et al. | 600/504 |
| 2002/0172323 A1 * | 11/2002 | Karellas et al. | 378/51 |
| 2002/0173725 A1 * | 11/2002 | Rock et al. | 600/500 |
| 2004/0225255 A1 * | 11/2004 | Ono | 604/65 |
| 2006/0178616 A1 * | 8/2006 | Hartman et al. | 604/65 |

FOREIGN PATENT DOCUMENTS

| | | |
|---|---|---|
| WO | WO 99/26686 | 6/1999 |

* cited by examiner

EXTRAVASATION DETECTOR

CROSS REFERENCE TO RELATED APPLICATIONS

This application claims the benefit of U.S. Provisional Application No. 60/432,256, filed Dec. 11, 2002, the content of which is incorporated herein by reference, and claims the right to priority based on United Kingdom Application No. 0228770.4, filed Dec. 10, 2002.

The present invention relates to an apparatus and method for detecting extravasation.

There are numerous medical procedures in which it is necessary to infuse a substance into a blood vessel. Typically a cannula is inserted into a vein and the substance is fed to this via a flexible tube. The substance may be blood, saline, a drug, a contrast medium, etc. In many cases it is desirable that the infusion occurs slowly and so the substance is simply gravity fed. However, there are circumstances in which it is necessary to force the substance into the blood vessel.

One example is the infusion of a contrast medium used in conjunction with an imaging system such as angiography, computed tomography (CT), ultrasound or MRI. In many applications of these procedures it is necessary to infuse a contrast medium into the part of the body that is to be imaged. The medium must often be infused at a comparatively high rate for effective results to be achieved. As a consequence, in recent years, a number of injector-actuated syringes and power injectors for pressurized injection of contrast medium have been developed.

However, whilst such devices are valuable and effective, they do create a risk of extravasation. Extravasation is the accidental infusion of fluid such as contrast media into tissue surrounding a blood vessel, rather than into the blood vessel itself. The causes for extravasation vary. Fragile vasculature or valve disease may cause physiological limitations to the ability of the blood vessel to tolerate the high rate of fluid administration used in some procedures. In computed tomography, for example, contrast injection flow rates can be in the range of 0.1 to 10 ml/s. and so a failure of the vessel may occur. Alternatively, operator error may lead to inappropriate needle placement and patient movement may cause the infusing needle to be pulled from the intended vessel or cause the needle to be pushed through the wall of the vessel.

Extravasation of contrast media during intravenous injection is a potential serious complication that might necessitate surgical drainage of the affected region. Even though the incidence rate is low, it is considered to be a major concern and is associated with local pain and possibly necrosis of the tissue. If it occurs during an imaging procedure it is often necessary for the examination to be aborted and repeated at a later stage. It is therefore important to be able to detect extravasation quickly and reliably so that infusion may then be stopped. Other substances may have more serious effects. Chemotherapy drugs can be toxic to tissue if not diluted by blood flow.

Several extravasation detection techniques are known in the art. Two simple and very useful techniques for detecting extravasation are palpation of the patient in the vicinity of the injection site and simple visual observation of the vicinity of the injection site by a trained health care provider.

In the palpation technique, the health care provider manually senses swelling of tissue near the injection resulting from extravasation. By visual observation, it is also sometimes possible to observe directly any swelling of the skin in the vicinity of an injection site resulting from extravasation.

There have been a number of attempts to improve the detection of extravasation. For example, mercury strain gauge plethysmographs measure the volume change resulting from venous blood flow in a cross sectional area of a limb of a patient in order to detect a change in volume of a limb or digit as a result of extravasation.

Photo-plethysmographs measure the optical scattering properties of capillary blood to detect the presence of extravasated fluids in tissue. WO 99/15074 provides a sensor pad having a surface that is placed against a patient. A light source is also provided and a detector on the pad optically detects extravasation by detecting light that is reflected, scattered, etc.

U.S. Pat. No. 4,647,281 discloses subcutaneous temperature sensing of extravasation using a microwave radiometer. The temperature of the subcutaneous tissue where the fluid is injected is compared to that of the injected fluid.

It is also known to detect extravasation by measuring changes in the electrical impedance. Injection fluid in the tissue of the patient also changes the electrical impedance properties of the tissue. Thus, an impedance change of a certain level in the vicinity of the injection site is interpreted as being due to extravasation. WO 99/26686 discloses an electrode patch for attachment to the skin of a patient. It has elongate pick-up electrodes and energizing electrodes. The patch is used to monitor tissue impedance during the procedure and this is compared to a baseline level.

A disadvantage of such devices is that it can be difficult to maintain good electrical contact with the skin of the patient. Also, the location of the patch makes it more difficult to carry out palpation or visual inspection. A similar problem arises with the other prior art detectors. In order to address this problem, U.S. Pat. No. 6,408,204 proposes an apparatus that may be positioned so as not to interfere with palpation or visual inspection. An energy source and a receiver are positioned between a first layer of high dielectric material and a second layer of low dielectric material. If extravasation occurs, as noted above, there is a change in the bulk electrical properties of the tissue. The receiver measures a signal resulting from changes in the energy supplied to the tissue by the energy source.

According to the present invention there is provided a method of detecting extravasation during the infusion of a substance into a blood vessel comprising the step of detecting a change in the flow velocity within the blood vessel downstream of the point of infusion.

Thus, unlike the prior art techniques the present invention is not based on volume changes of tissue induced by extravasation, but on direct monitoring of the increased flow velocity within the blood vessel induced by the infusion. The lack of a velocity increase indicates that extravasation has occurred. Since the increase in flow velocity should occur almost immediately infusion commences, this method gives the operator an early warning if a problem occurs.

It can be difficult to precisely locate the blood vessel downstream of the point of infusion. Therefore in a preferred embodiment of the invention, an array of detector elements is arranged substantially transverse to the direction of flow of the blood vessel so that at least one element of the array will be located over the vessel. The signal from each detector element varies depending on whether the detector element is located over the blood vessel or over ordinary tissue. This has the advantage that the accuracy with which the detector must be placed is reduced. At least one element of the array will be located over the vessel, and so it is not necessary to precisely locate the blood vessel at the point of measurement prior to commencing the measurement. Instead, a change in flow velocity will be detected by whichever element or elements of the array are located over the blood vessel.

The change in flow velocity could be detected by measuring the flow velocity at a single point downstream of the point of infusion. In one preferred embodiment however, the flow velocity within the blood vessel is measured at a plurality of points spaced apart along the extent of the vessel and positioned downstream of the point of infusion. This has the advantage of enabling a user to determine the approximate position within the vessel at which extravasation has occurred.

Although the method of the invention is applicable to any infusion of a substance that causes a detectable increase in blood flow velocity, it is of particular use where the infusion is at a high rate where the greatest risk of extravasation occurs. The rates of infusion may be over 5 ml/s and sometimes over 10 ml/s. Thus, the invention is of particular application to venous infusions such as contrast agents. The invention may therefore be incorporated as part of a process of generating a medical image.

The invention could just be applied when the infusion is commenced, or when the rate of infusion is increased, these being times when a problem is most likely to occur. However, as noted above, extravasation may be caused by patient movement and so preferably blood flow velocity changes are continuously or repeatedly monitored during the procedure.

In a simple form of the invention, a change in velocity may be noted by an operator who can then stop the infusion. However, it is preferable that the method further comprises the provision of a notification that extravasation has occurred and most preferably there may be automatic shutdown of the infusion in response to the detection of extravasation.

The invention also extends to an apparatus for detecting extravasation during the infusion of a substance into a blood vessel comprising a detector for detecting a change in the flow velocity within the blood vessel downstream of the point of infusion, the apparatus being arranged to provide an output signal when extravasation occurs.

The output signal may be a notification such as an alarm. More preferably it comprises a control signal to control the infusion. The output signal need not be "high" to indicate extravasation. Indeed, it may be preferable to use a fail-safe system in which a "high" output indicates an increased velocity and therefore that extravasation has not occurred. Thus, if the "high" signal is lost, either due to extravasation or equipment failure, the infusion can be stopped.

Any suitable method of detecting flow velocity may be applied, but it is believed that the most effective technique is ultrasound Doppler. Thus, the detector is preferably an ultrasound Doppler probe which may consist of a single transducer element and more preferably consists of an array of individual transducer elements adapted to be arranged substantially transverse to the direction of flow of the blood vessel so that the position of the blood vessel can be detected and/or the change in flow velocity in the blood vessel can be detected without first knowing the precise location of the blood vessel. In another embodiment of the invention, a plurality of individual transducer elements (or arrays of transducer elements) are spaced apart along the direction of flow of the blood vessel to form an array (or a two dimensional array) of transducer elements which can track the direction of a blood vessel in use. The probe may be located against the skin of a patient proximate to a vein into which the infusion is being made and downstream of the infusion site. The probe is preferably fixed to the patient's skin using an adhesive. In accordance with standard practice, a coupling medium (ultrasound gel) should preferably be applied to the patient's skin under the transducer elements.

The probe may be connected to a display unit in the conventional manner in which case increases in flow velocity will be visible conventionally as bright patches on the display. These may be detected using conventional techniques, for example by comparing pixel brightness in a preselected region on the display. Alternatively, the display can be dispensed with and a direct indication of velocity produced. Normally the velocity of the infusion will be significantly higher than any other velocity of flow in the region concerned and so precise measurement is not required.

An analogue signal voltage which is generally proportional to the detected flow velocity may be provided as the output from the detector. This could be used to drive a simply calibrated meter. Additionally or alternatively the voltage may be compared to a threshold voltage such that when this is exceeded an indication is provided that extravasation has (or has not) occurred.

In many applications it may be preferable to use a digital system. If the output from the detector is not in digital form then it may be converted using a conventional analogue-digital converter. The output may then be fed to a processor such as a personal computer or a custom processor incorporated into the apparatus.

Regardless of the system used, an output control signal may then be provided to control the infusion pump. In a simple form this may operate a relay to cut the power to the pump, or if the pump is computer controlled it may be a digital control signal. Alternatively, a valve arrangement may be used to prevent flow to the vein.

It will be appreciated that the invention extends to a system for giving an infusion comprising an infusion pump arranged to infuse a substance into a blood vessel and an extravasation detector according to the apparatus defined above wherein the detector apparatus is arranged to control the infusion pump. The invention also extends to a method of giving such an infusion comprising the use of such apparatus.

Certain embodiments of the invention will now be described, by way of example only, and with reference to the accompanying drawings in which:—

Figure 1:
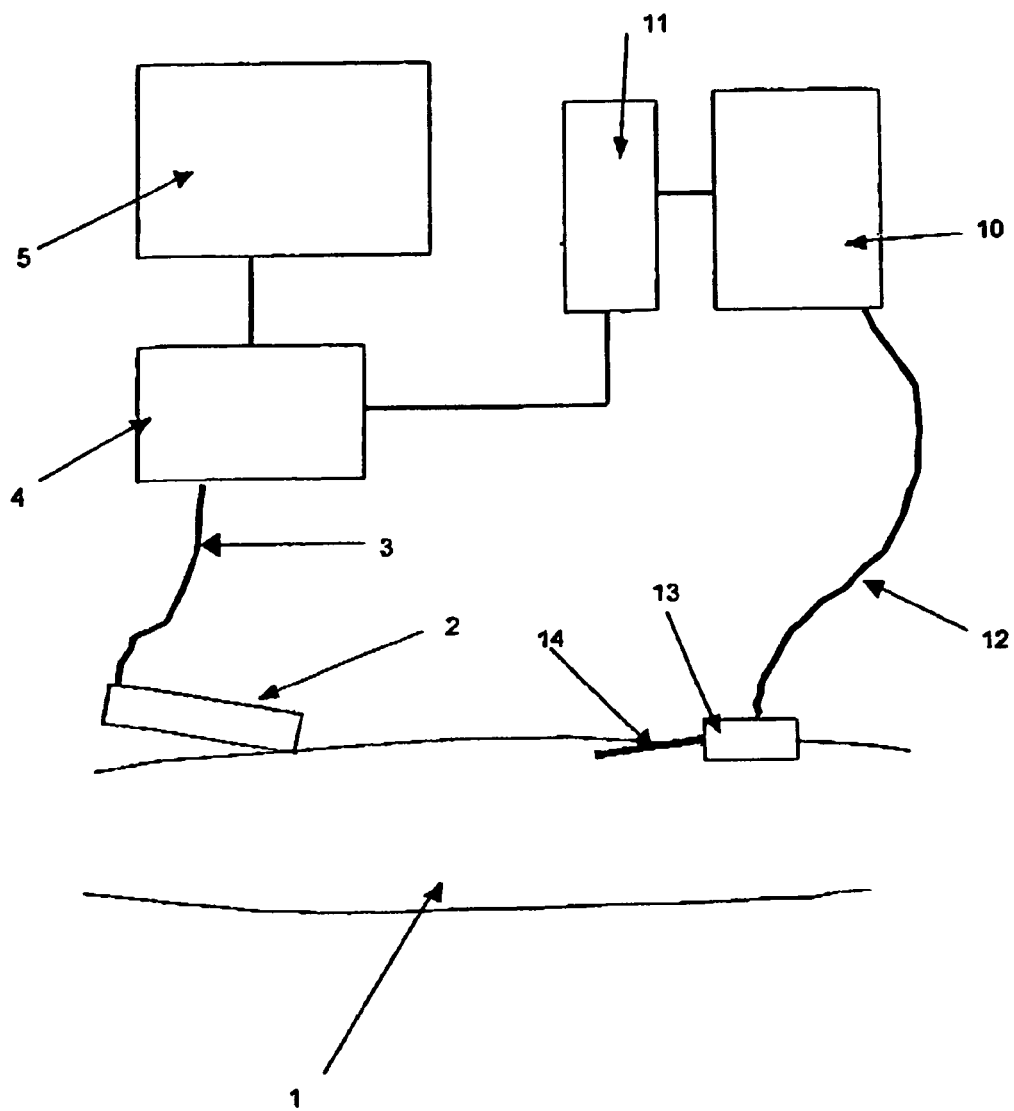
FIG. 1 is a schematic view of a first embodiment of the invention.

In FIG. 1 a patient's arm is illustrated at 1. A contrast medium is being infused into the patient from a pump 10. The pump is controlled by an electronic pump controller 11, which varies the pump speed as required and starts and stops it.

The contrast medium flows via flexible tube 12 to cannula arrangement 13, which comprises a connector for connection to the flexible tube, and a fine bore tube 14 which has been inserted into a vein in the known manner.

Ultrasound Doppler probe 2 is placed above the same vein and a convenient distance downstream so as to be clear of the infusion site. The Doppler probe consists of a single transducer element 2 which in use is placed at an angle to the vein to create and detect a Doppler shift from the flow. The probe 2 is connected via a flexible lead 3 to a processor unit 4. This converts the output from the probe 2 into a form that may be displayed as an image on display unit 5 in the conventional manner. In addition it provides a digital signal proportional to the flow velocity detected by the probe 2. This value is then also displayed on display 5. In addition, the unit 4 determines whether the velocity corresponds to a flow of contrast medium along the vein.

When the infusion is to commence, the operator sets the desired infusion rate by inputting it into the pump controller 11 and then inputs a start signal into unit 4 by pressing a key (not shown). This in turn transmits a start signal to the pump controller 11 which energises the pump and causes it to run at the desired speed.

The processor unit 4 then checks the flow velocity as described above. If it is not satisfactory within a predetermined short period of time the infusion will be stopped.

Figure 4:
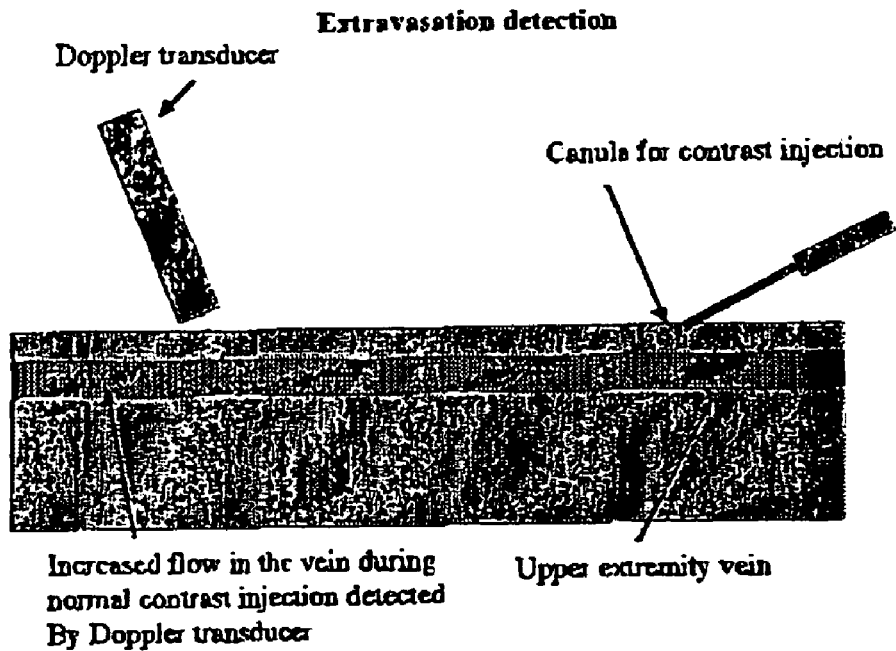
FIG. 4 is a diagram illustrating the use of the embodiment of FIG. 1 where no extravasation has occurred.

As may be seen from FIG. 4, if the cannula is properly sited and the contrast medium flows as desired along the vein, this will lead to an increased flow velocity in the vein. This is detected by ultrasound probe 2 and, as described above, the processor unit 4 will therefore determine that no extravasation has occurred. It will therefore continue to send a "pump" signal to pump controller 11.

Figure 5:
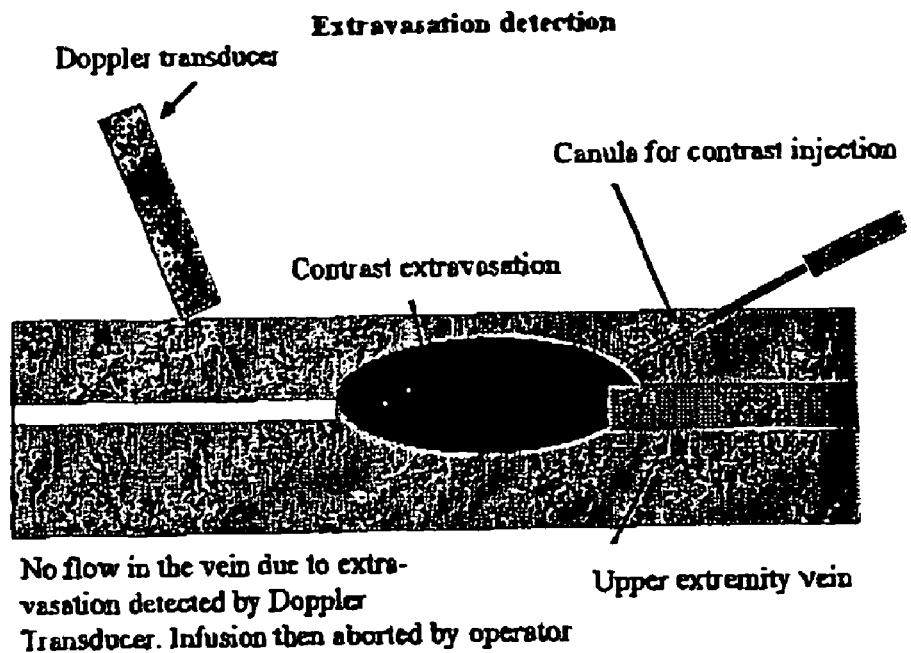
FIG. 5 is a diagram illustrating the use of the embodiment of FIG. 1 where extravasation has occurred.

FIG. 5 shows the situation that might occur when there is extravasation of contrast medium and consequently no flow in the vein. This results in a low or zero velocity output from the probe 2 from which the processor unit 4 determines that extravasation has occurred. It therefore immediately sends a "stop" signal to pump controller 11 which stops pump 10. In this way, the infusion may be stopped almost as soon as the problem occurs with the result that only a small amount of contrast medium enters the tissue surrounding the vein.

Although the situation illustrated in FIG. 5 is most likely to occur when the infusion commences, the processor unit constantly monitors the output from the probe 2 throughout the infusion procedure and can stop the pump at any time.

Figure 2:
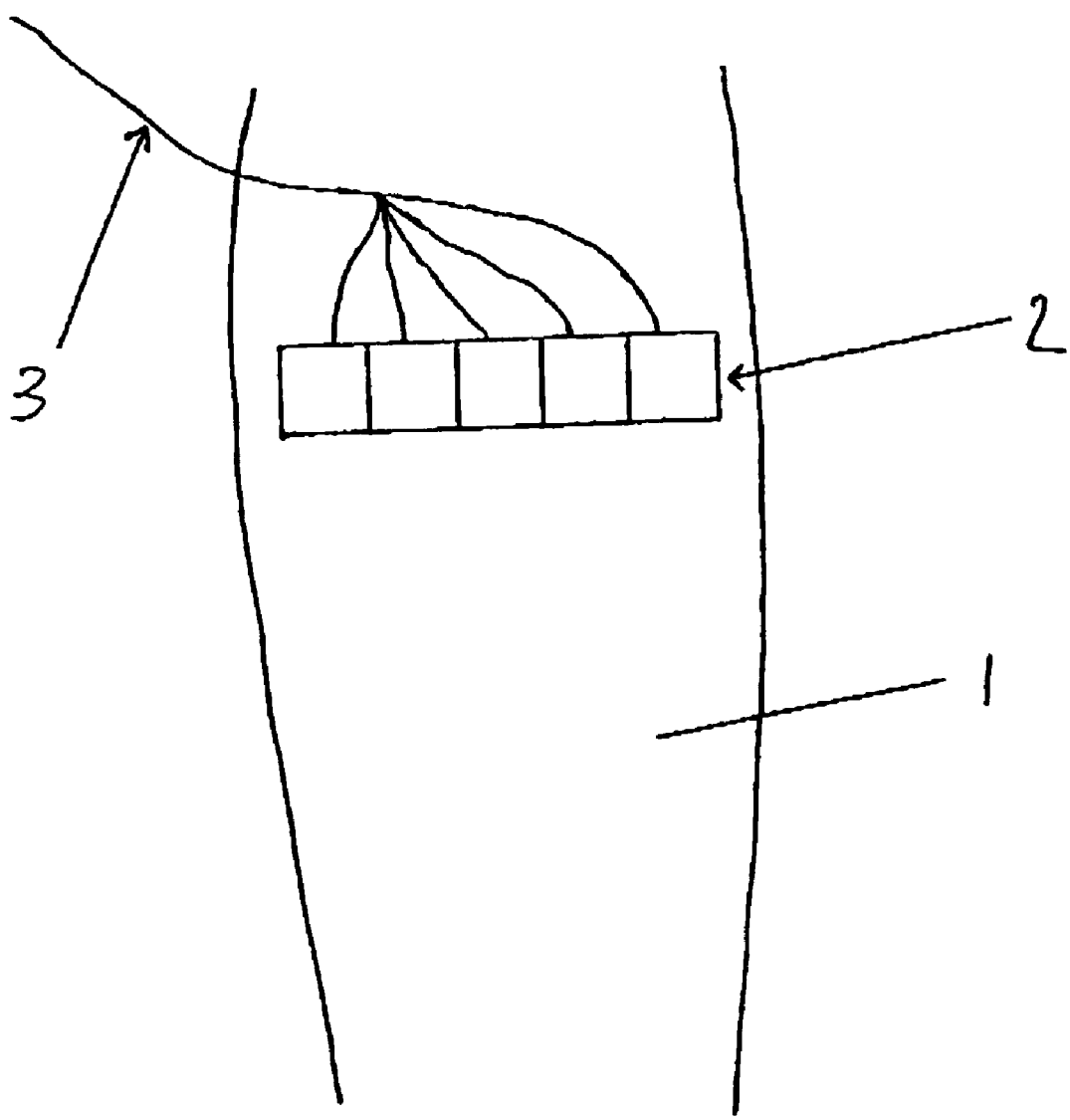
FIG. 2 is a schematic view of a modified version of the FIG. 1 embodiment.

FIG. 2 shows a modified version of the embodiment of FIG. 1 in which an array of individual transducer elements is provided and in use is arranged on the patient's arm substantially transverse to the direction of flow of the vein (i.e. normal to the plane of FIG. 1). Thus, the precise location of the vein need not be known prior to measurement. The signal from each transducer varies depending upon whether it is situated above tissue or above a vein (a Doppler shift will be detected if the transducer is directed towards moving fluid such as blood flowing in a vein). By monitoring the signals received by each transducer element in the array, the location of the vein can be detected. Once it has been determined which transducer elements are situated over the vein, those transducer elements can be monitored for changes in the flow velocity within the vein and hence it can be determined whether or not extravasation has occurred.

Figure 3:
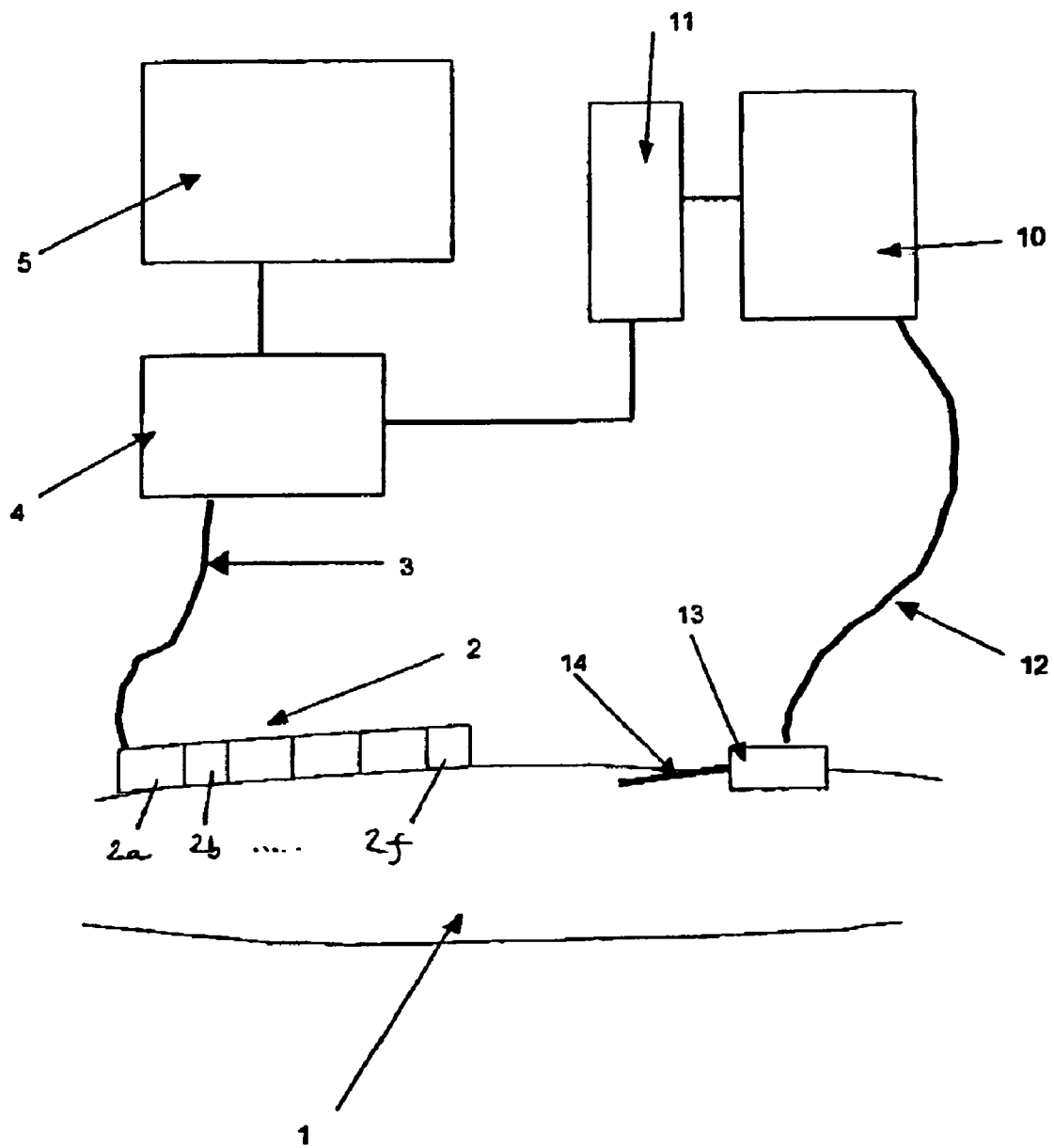
FIG. 3 is a schematic view of an alternative embodiment of the invention.

FIG. 3 shows an alternative embodiment of the invention in which the Doppler probe 2 consists of a number of individual transducer elements 2a-2f. These transducer elements are spaced at regular intervals to form an array which can be placed on a patient's arm downstream of cannula arrangement 13 to extend along the vein in the flow direction.

In a modified version of the embodiment of FIG. 3 (not illustrated), a two dimensional array of individual transducer elements is provided such that the elements extend both substantially transverse and substantially parallel to the direction of flow of the vein. In this way, the precise location of the vein need not be known at each measurement point before commencing measurement.

Instead, as previously described, it is determined which elements of the array are situated over the vein and those elements are monitored for changes in the flow velocity within the vein. Each such transducer element measures the flow rate at a respective point in the vein and this information is provided to the processor unit 4. The processor can therefore determine the approximate position along the vein at which extravasation has occurred. Thus for example, if the flow velocity measured at elements 2a to 2c corresponds to the flow velocity of the contrast medium within the vein but the velocity measured at element 2d does not, the processor determines that extravasation has occurred in the region of transducer element 2d. The remaining parts shown in FIG. 3 correspond to those shown in FIG. 1 and so are not described again here.

The invention claimed is:

1. A method of detecting extravasation during a procedure infusing a substance into a blood vessel, comprising the steps of infusing a substance into the blood vessel;
    generating a first signal proportional to a flow velocity within the blood vessel downstream of the point of infusion, at a first time;
    generating a second signal proportional to the flow velocity within the blood vessel downstream of the point of infusion, at a second time;
    generating a third signal representing an increase in flow velocity, based on the first and second signals; and
    generating a fourth signal indicating extravasation if an increase in flow velocity represented by the third signal is less than a threshold value.

2. A method as claimed in claim 1, wherein an array of detector elements is arranged substantially transverse to the direction of flow of the blood vessel downstream of the point of infusion so as to locate at least one of said array of detector elements over the vessel.

3. A method as claimed in claim 1 or 2, wherein the flow velocity within the blood vessel is measured at a plurality of points spaced apart along the vessel and downstream of the point of infusion.

4. A method as claimed in claim 1, wherein the infusion is a venous infusion of a contrast agent.

5. A method as claimed in claim 1, wherein a change in the flow velocity is continuously or repeatedly monitored.

6. A method as claimed in claim 1, further comprising the provision of a notification that extravasation has occurred.

7. A method as claimed in claim 1, further comprising an automatic shutdown of the infusion in response to the detection of extravasation.

8. A method as claimed in claim 1, wherein extravasation is indicated by a lack of velocity increase after the intended infusion has commenced.

9. A method as claimed in claim 2, wherein the detector elements are ultrasound transducer elements.

10. An apparatus for detecting extravasation during an intended infusion of a substance into a blood vessel at a point of infusion, comprising:
    a detector for generating a flow signal corresponding to a flow velocity within the blood vessel downstream of the point of infusion; and
    a controller coupled to the detector and configured to:
        determine a first flow velocity at a first time based on the flow signal;
        determine a second flow velocity at a second time during infusion based on the flow signal; and
        generate an output signal indicating occurrence of extravasation based on the difference between the first flow velocity and the second flow velocity.

11. An apparatus as claimed in claim 10, wherein the detector comprises an array of detector elements that are arranged substantially transverse to the direction of flow of the blood vessel so as to locate at least one of said array of detector elements over the vessel.

12. An apparatus as claimed in claim 10 or 11, wherein the detector measures the flow velocity within the blood vessel at a plurality of points spaced apart along the vessel and downstream of the point of infusion.

13. An apparatus as claimed in claim 10, wherein the output signal is a notification or alarm.

14. An apparatus as claimed in claim 10, wherein the output signal is a control signal to control the infusion.

15. An apparatus as claimed in claim 10, wherein the detector is an ultrasound Doppler probe.

16. An apparatus as claimed in claim 11, wherein the detector elements are ultrasound transducer elements.

17. A system for giving an infusion comprising an infusion pump arranged to infuse a substance into a blood vessel and an extravasation detector according to claim 10, wherein the detector apparatus is arranged to control the infusion pump.

18. An apparatus as claimed in claim 10, wherein the apparatus is arranged to provide an output signal when there is a lack of velocity increase after the intended infusion has commenced.

* * * * *